(12) United States Patent
Wang et al.

(10) Patent No.: US 7,186,518 B2
(45) Date of Patent: Mar. 6, 2007

(54) METHOD AND COMPOSITION USEFUL FOR DETERMINING FK 506

(75) Inventors: Chengrong Wang, Glen Mills, PA (US); Tie Q. Wei, Bear, DE (US); Zhu Teng, Boothwyn, PA (US)

(73) Assignee: Dade Behring Inc., Deerfield, IL (US)

( * ) Notice: Subject to any disclaimer, the term of this patent is extended or adjusted under 35 U.S.C. 154(b) by 193 days.

(21) Appl. No.: 10/719,868

(22) Filed: Nov. 21, 2003

(65) Prior Publication Data

US 2005/0112778 A1  May 26, 2005

(51) Int. Cl.
*G01N 33/535* (2006.01)
*G01N 33/533* (2006.01)
*G01N 33/534* (2006.01)
*G01N 33/553* (2006.01)

(52) U.S. Cl. .................... 435/7.92; 435/7.93; 436/526; 436/544; 436/545; 436/546; 436/815; 436/825

(58) Field of Classification Search ................ 540/455; 436/526, 546, 815, 544, 545, 825; 435/7.92, 435/7.93
See application file for complete search history.

(56) References Cited

U.S. PATENT DOCUMENTS

| | | |
|---|---|---|
| 4,434,236 A | 2/1984 | Freytag |
| 5,227,304 A | 7/1993 | Wong |
| 5,338,684 A | 8/1994 | Grenier et al. |
| 5,352,671 A | 10/1994 | Baumann et al. |
| 5,373,014 A | 12/1994 | Failli et al. |
| 5,532,137 A | 7/1996 | Niwa et al. |
| 5,576,183 A | 11/1996 | Kobayashi et al. |
| 5,635,406 A | 6/1997 | Grenier et al. |
| 5,650,288 A | 7/1997 | MacFarlane et al. |
| 5,665,727 A * | 9/1997 | Grassberger et al. ....... 514/291 |
| 5,672,605 A | 9/1997 | Or et al. |
| 5,736,401 A | 4/1998 | Grenier et al. |
| 5,780,307 A | 7/1998 | Soldin |
| 6,166,011 A | 12/2000 | Wythes et al. |
| 6,187,547 B1 | 2/2001 | Legay et al. |
| 6,338,946 B1 * | 1/2002 | Kobayashi et al. .......... 435/7.1 |

FOREIGN PATENT DOCUMENTS

| | | | |
|---|---|---|---|
| EP | 0 293 892 B1 | | 12/1993 |
| EP | 0 717 850 B1 | | 5/1997 |
| WO | 91/02736 | * | 3/1991 |
| WO | WO 91/13899 | | 3/1991 |
| WO | 91/17754 | * | 11/1991 |
| WO | 92/00313 | * | 1/1992 |

OTHER PUBLICATIONS

T. Wei, G. Parker, C. R. Wang. Development of a fully automated tacrolimus method for the Dimension® clinical chemistry system. *Clin Chem.* (2001) 47(6), A75.
DiaSorin, Catalog No. 32400; PRO-Trac™ II Tacrolimus ELISA Kit; Instruction Manual.

* cited by examiner

*Primary Examiner*—Mary E. Ceperley
(74) *Attorney, Agent, or Firm*—Cynthia G. Tymeson; Robert N. Carpenter

(57) ABSTRACT

New derivatives of FK 506 are disclosed. These new derivatives and other derivatives that are useful for determining the levels of FK 506 in a sample are also provided as are assay procedures and kits for use in determining the levels of FK 506 or other macrophilin binding substances in blood, particularly un-extracted blood in the presence of specific binding proteins for FK 506.

8 Claims, 1 Drawing Sheet

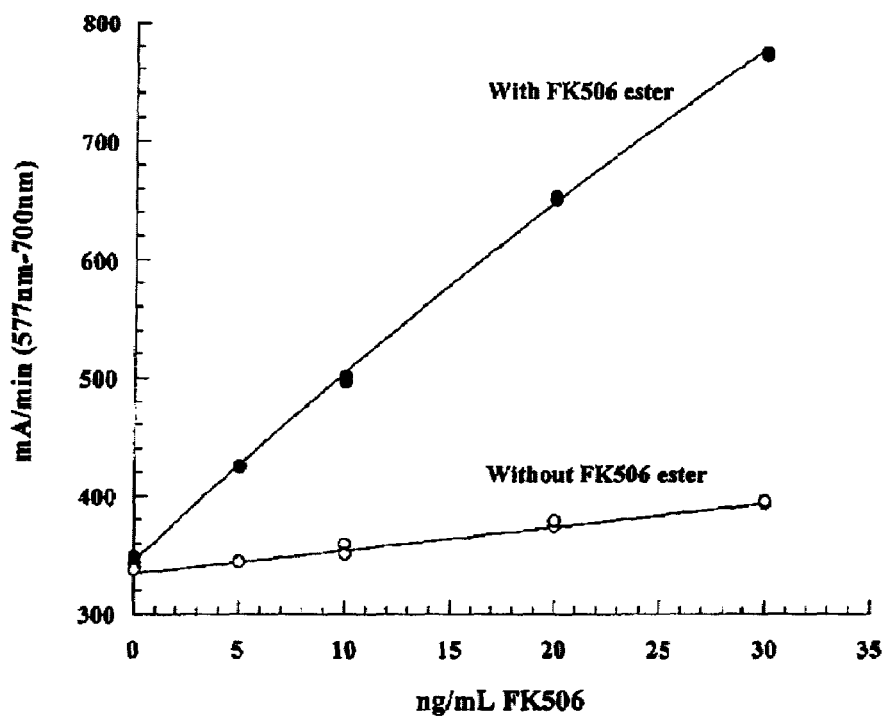
Figure 1. Representative calibration curves representing the DIMENSION® assay treated with or without the FK506 carbamate pretreatment.

METHOD AND COMPOSITION USEFUL FOR DETERMINING FK 506

BACKGROUND OF THE INVENTION

This invention relates to an assay procedure and kit for use in determining the levels of FK 506 or other macrophilin binding substances in blood, particularly un-extracted blood in the presence of specific binding proteins for FK 506. The method uses derivatives of FK 506 to displace the FK 506 from specific binding proteins for FK 506. The invention also relates to novel compounds that are useful for displacing FK 506 from its specific binding protein.

FK 506 (or tacrolimus) is a cyclic, poly-N-methylated undecapeptide, possessing immunosuppressive activity. FK 506 is a macrolide immunosuppressant that is produced by *Streptomyces tsukubaensis* No 9993. The structure of FK 506 is shown in FIG. 1.

Formula 1

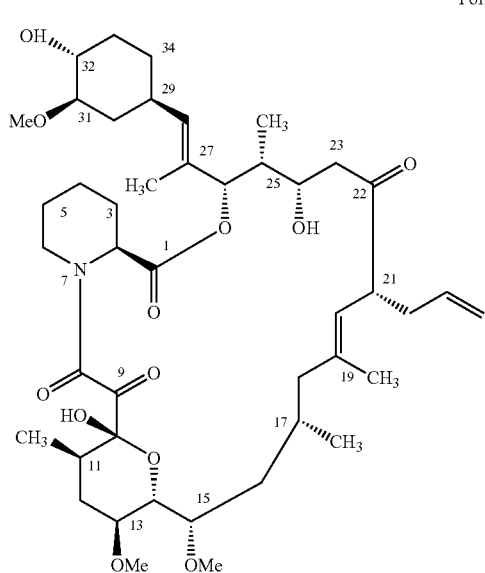

Also a large number of related compounds which retain the basic structure and immunological properties of FK 506 are also known. These compounds are described in a number of publications, for example EP 184162, EP 315973, EP 323042, EP 423714, EP 427680, EP 465426, EP 474126, WO 91/13889, WO 91/19495, EP 484936, EP 532088, WO 93/5059 and the like.

FK 506 compounds are used, for example, in the prevention of transplant rejection. However these FK 506 compounds have side effects at higher doses and therefore their concentration in the blood must be kept within certain therapeutic ranges. Further, bioavailabilities and metabolic conversion rates tend to be patient specific and hence dosing is patient specific. The potency and the spectrum of toxicity of FK 506 require sensitive, reproducible and reliable methods for monitoring the blood concentration of these compounds. It is therefore necessary to monitor the concentration of these immunosuppressant drugs in the blood at regular intervals. Rapamycin and cyclosporin are other compounds used in the prevention of transplant rejection. These drugs may be used singly or in combination.

It has been found that a portion of the FK 506 compound present in blood exists in the form of a FK 506 immunophilin complex. Immunophilins are a family of intracellular binding proteins that bind cyclosporins, rapamycins or FK 506 compounds. Two distinct families of immunophilins are presently known; cyclophilins which bind to cyclosporins and macrophilins which bind to rapamycins (sirolimus) and its derivatives such as everolimus and FK 506 compounds. The structures of certain immunophilins are described in Walkinshaw et al; 1992; *Transplantation Proceedings*, 24, 4(2), 8–13. The macrophilins which bind to FK 506 are called FK 506 binding proteins. Five members, thus far, have been reported: FKBP-12, FKBP-12.6, FKB-13, FKBP-25 and FKBP-52.

Given the importance of cyclosporins, rapamycins and FK 506 compounds as pharmaceuticals, there is a need for simple, sensitive assays to determine their concentrations in blood.

For FK 506, specific monoclonal antibodies have been developed and assay procedures based on the antibodies provided. WO 95/07468, U.S. Pat. No. 5,532,137. However, these assay procedures available require the blood or plasma sample first be extracted with a solvent (such as methanol) which is then removed by evaporation or dilution to free the FK 506 from its binding protein. The antibody is then added to the sample and the FK 506:Ab complex is detected. The assay procedure based on the specific monoclonal antibody works well but the need for the extraction step and the subsequent removal of the solvent can result in the assay becoming less sensitive and less precise if care is not taken. Therefore the assay must be carried out by skilled technicians and is a time consuming procedure.

It is known from studies conducted in vitro, excess concentrations of rapamycin prevent the effects of FK 506 by displacing FK 506 from FKBP's. Fruman, David et al., *Calcineurin Phosphatase activity in T lymphocytes is inhibited by FK 506 and cyclosporin A*, PNAS (1992) 89(9), 3683–90. Further, EP 717850 discloses an assay method for FK 506 that uses a binding-competitor, namely rapamycin, to displace FK 506 from its binding protein. Thus, an extraction step is not needed. However, since rapamycin, FK 506 and cyclosporin can be used singly or in combination, it is preferred that the binding-competitor be a different compound than one of the immunosuppressive drugs so that the amount of binding competitor in the sample can be controlled.

SUMMARY OF THE INVENTION

The present invention relates to derivatives of FK 506. These derivatives can act as a binding competitor to displace FK 506 or rapamycin from its immunophilin complexes. The derivatives of the present invention are also referred to herein as binding competitors.

In addition, this invention provides an assay procedure for determining the concentration of FK 506 or rapamycin in a sample of blood or other fluid; the procedure comprising adding a binding competitor that displaces FK 506 or rapamycin from immunosuppressant-immunophilin complexes in the sample; adding a receptor that binds to the pharmaceutical but not significantly to the binding competitor; separating the receptor-pharmaceutical complex from the sample; and determining the amount of the pharmaceutical.

Another aspect of the present invention relates to reagents and kits useful for displacing FK 506 or rapamycin from immunophilin complexes.

DETAILED DESCRIPTION OF THE INVENTION

The FK 506 derivatives of the present invention are prepared by derivatizing tacrolimus. The derivatives are formed at the —OH groups of tacrolimus, at C-32 and/or C-24 to form ether, (FK-OR), ester

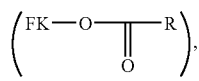

or carbamate linkages

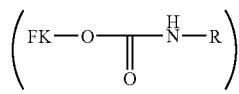

providing derivatives of FK-506 at either or both of these positions. In one aspect both the C-32 and C-24 are derivatized and in another aspect the derivatives are di-carbamate derivatives. Thus, the substances of the present invention may be for example the derivatives exemplified in FIG. 2. R (at C-32) and R (at C-24) may be independently selected from alkyl or allyl groups from C1 to C25, either linear or branched or aromatic groups with or without substitutions. In addition the alkyl, allyl or aromatic group may contain other functional groups such as ester, ethers, amides, acyl, amines, hydroxyl, sulfonates, phosphates, sulfates, phosphonate groups and the like. R may not be H. R' may be H. Many of these derivatives are known in the art. See, for instance, U.S. Pat. No. 5,665,727.

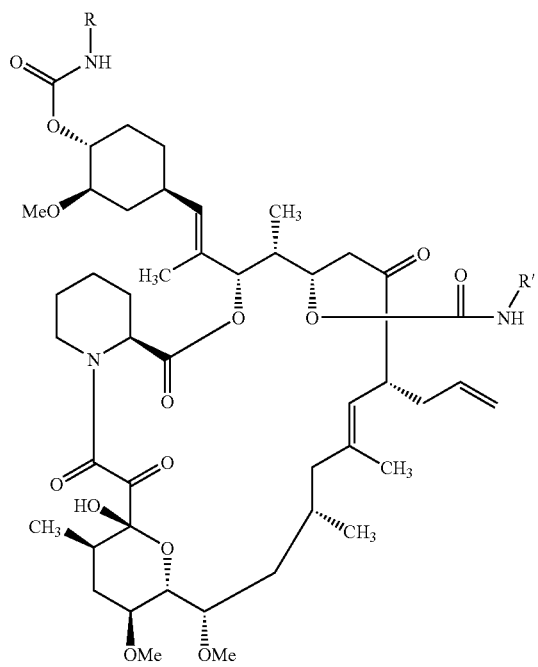

Formula 3

Other aspects of the invention are shown in FIG. 3 above. These carbamate derivatives are derivatized at both C-24 and C-32. R and R' may be independently selected from alkyl, allyl, acyl, aryl in addition the alkyl, allyl, or aromatic group may contain other functional groups such as ester, ethers, amides, acyl, sulfonates, phosphates, sulfates, phosphonate groups and the like. R may be H. R' may be H.

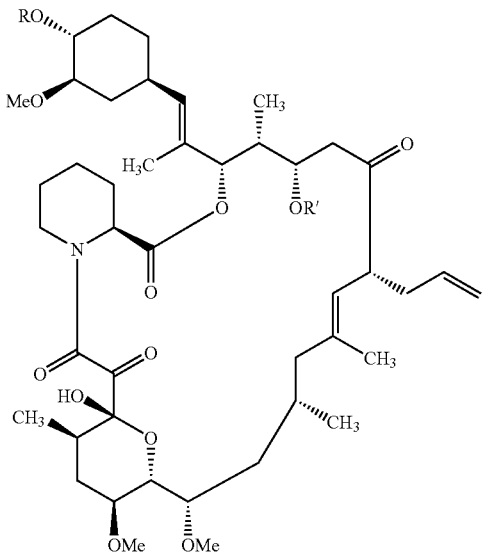

Formula 2

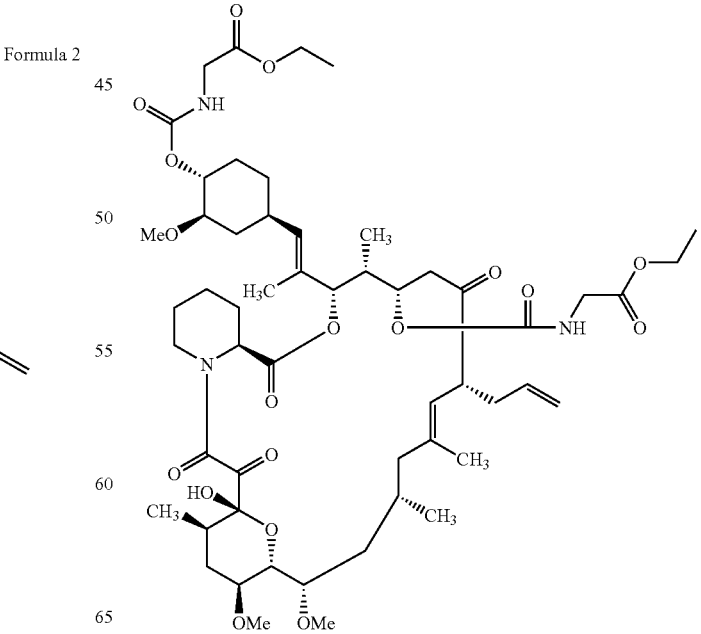

Formula 4

A particular carbamate derivative is shown above in FIG. 4. This carbamate derivative is derivatized at both C-24 and C-32. In this example R and R' are identical.

The FK-506 derivatives of the present invention may be prepared by methods known in the art and are useful in immunoassays as binding competitors of FK-506 or rapamycin.

In the method of the present invention, a binding competitor of FK-506 or rapamycin is added to the sample to release any FK 506 or rapamycin from its complex. The binding competitor is an FK-506 derivative or analog as shown in FIGS. 2, 3 and 4. The method of this invention uses receptors that bind to the pharmaceutical but not significantly to the binding competitor. The receptor, which recognizes and binds to FK 506 (or rapamycin if the pharmaceutical to be measured is rapamycin), may be any specific binding compound as is used in conventional assays, e.g. polyclonal, monoclonal, recombinant antibodies, or antibody fragments. It is preferably a monoclonal antibody.

Once the FK 506 is released from the complex, the amount of the FK 506 bound to the receptor may be determined using any assay method, preferably a monoclonal antibody based assay, e.g. a competitive assay measuring the ability of the pharmaceutical to compete for binding to the antibody or receptor, or a noncompetitive assay, likewise in an assay for rapamycin. A competitive assay preferably uses, e.g. labeled FK 506 (tracer) as competitor for the antibody, in the presence and absence of the test sample. The tracer may be labeled with a label capable of providing a suitable signal, e.g. radioactive, fluorescent, luminescent or colorimetric signal as is conventional in the art. Alternatively, the competitor for the receptor may be unlabeled pharmaceutical (optionally the pharmaceutical-protein immunogenic conjugate used to raise the antibody) coated onto the surface of the test chamber, e.g. in an enzyme-linked immunosorbent assay (ELISA) or in a system where the antibody for the pharmaceutical is itself labeled. The antibody or receptor may be free in the test solution or coated onto the wall of the test chamber, depending on the assay system used. In a competitive assay, the signal (e.g. amount of tracer bound to antibody or receptor) is inversely proportional to the amount of pharmaceutical in the test sample. Standard solutions containing known concentrations of FK 506 may be used to standardize the assay as is conventional, likewise for rapamycin if that is the pharmaceutical of interest.

A receptor that binds to FK 506 but not significantly to the binding competitor, means that the extent of receptor cross reactivity between FK 506 and the binding competitor is not sufficient to significantly affect the sensitivity of the assay or the clinical significance of assay results. The precise amount of cross reactivity between the binding competitor and FK 506 (and/or the binding competitor and the tracer in a competitive assay) which can be tolerated of course varies to some extent on the relative affinity of the binding competitor to the immunophilin compared to FK 506: the higher the affinity, the lower the concentration needed to displace FK 506 and the greater receptor cross reactivity that can therefore be tolerated without affecting the accuracy of the assay. In practice, the significance of cross reactivity is best measured by comparing standard curves using different amounts of binding competitor; once the minimum concentration of binding competitor for displacement of FK 506 is reached, the standard curves should not vary significantly as the binding competitor concentration increased to the highest level contemplated for use in the assay, thereby demonstrating that any cross reactivity with the antibody is insignificant in the context of the assay (if there was cross reactivity with the antibody, the presence of high concentration of binding competitor would tend to inflate the observed measurement of drug levels because the assay would measure FK 506 plus binding competitor). The significance of any variation between the standard curves in the presence and absence of binding competitor can be assessed using standard statistical methods, e.g. a t-test. As a guideline, however, because the binding competitor is usually present in much higher concentration than FK 506 in the test sample, the receptor cross reactivity between the pharmaceutical and the binding competitor should be, e.g. below 1%, preferably below 0.1%, as measured in a competitive assay in buffer.

In the invention, the binding competitor is a compound that is a suitable derivative of FK 506 that binds to FK 506 binding proteins, in particular FK BP 12. Any suitable FK-506 compound derivatized at C-32 and/or C-24 that is able to displace the FK 506 or rapamycin compound may be used, preferably those compounds shown in FIG. 2. Examples competitors are shown in FIGS. 3 and 4. The binding competitor is also selected based on its solubility in aqueous based solutions. Preferred R and R' groups or functionalities impart hydrophilicity or water solubility to the binding competitor. Such functional groups or functionality can be a substituent having 1 to 50 or more atoms and can include a group having a phosphate, sulfonate, sulfate, amidines, phosphonates, carboxylates, hydroxyl (particularly polyols), amine, ethers, amides and the like.

To prepare the displacing reagent the FK-506 derivatives of the present invention are dissolved in organic solvent such as methanol or the like and formulated into a displacing reagent in an assay for the drug. For instance, to prepare a stock solution, an FK-506 ester derivatized at R-24 and/or R-32 is dissolved in methanol and further diluted with a buffer at about a neutral pH. The buffer may contain carrier proteins such as bovine serum albumin, gelatin, gamma globulin and the like, salts, preservatives, or detergents. A typical stock solution may have from 0.2 to 2 mM FK-506 ester. Typically to make the reagent, the stock solution would be diluted to the micro-molar range such as 1–100 µM in a buffer similar to the stock solution buffer or water. The typical effective ratio of FK-506 derivative over sample FK-506 used in an assay is about 200:1, but this effective ratio may range from 10–10,000:1.

In the assay a portion (e.g. 1–200 µL) of the displacing reagent is combined with a portion of (e.g. 1–200 µL) the liquid sample containing FK-506. The solution, typically whole blood for a patient sample, is incubated to release the FK-506 from the binding protein. Typically, and for convenience of the user, the incubation time is from about 0.5 to 5 minutes. Once the FK-506 is released from the binding protein it is accessible to the binding partner, such as an antibody, that is used for its detection.

Suitable FK 506 compound antibodies may be used for detection; certain specific antibodies, are described in EP-A 0 293 892. Where a competitive assay is used, the competitor for the antibody may be an FK 506 compound bound to a solid phase such as a bead, paper, test tube, assay plate or the like. The labeled derivative of FK 506 may be an enzyme-labeled derivative such as FK-506 labeled with beta galactosidase or alkaline phosphatase or other labeled derivative.

The assay procedure of the invention has the advantages that it may be carried out rapidly and simply using standard bioanalytical equipment to give accurate and reproducible results. Also, whole blood may be used without the need for extraction.

The invention also provides an assay kit suitable for detecting the amount of FK 506 in blood, the kit comprising a macrophilin binding competitor that displaces FK 506 from FK 506 complexes in the blood; and an antibody that binds to the pharmaceutical but not significantly to the macrophilin binding competitor. Preferably, the antibody is a monoclonal antibody that is specific to FK 506.

The same macrophilin binding competitor may be used in a similar manner to release rapamycin from the macrophilin.

The kit may further comprise an appropriately labeled tracer, standard and instructions for use. The label for the tracer may be any suitable label, e.g. a radioactive, fluorescent, chemiluminescent, enzymatic or calorimetric label. Where convenient, the components of the kit may be in lyophilized form.

Examples of the invention are now described, by way of example and not limitation. It will be apparent to one skilled in the art that variations in the precise concentrations of reagents and reaction conditions may be tolerated, so long as the variations are consistent from assay to assay. Other assay systems using binding competitor of the present invention to release FK 506 from the FK 506 complex are considered within the scope of the invention; once the FK 506 is freed from the complex, it may of course be measured in any conventional way.

EXAMPLE 1

Preparation of an FK-506 Carbamate Derivatives

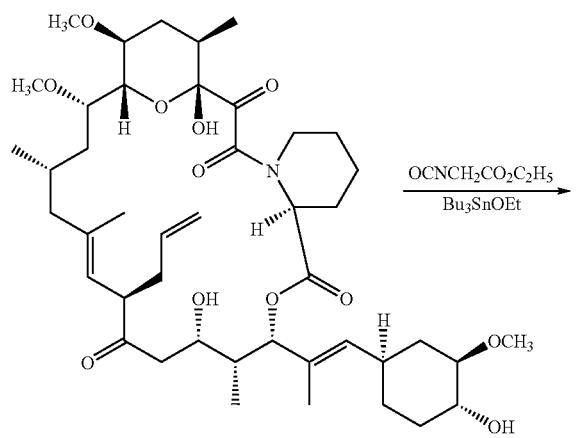

FK 506

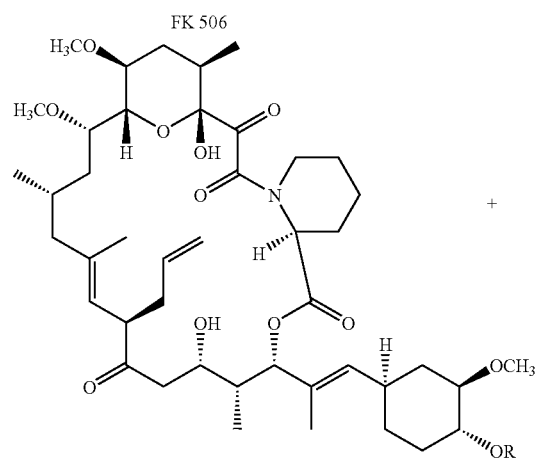

+

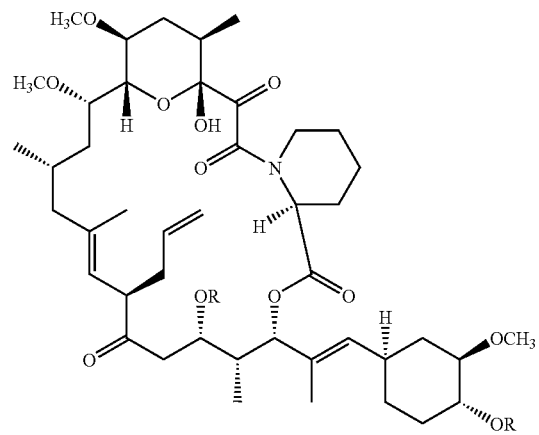

R = CONHCH$_2$COOC$_2$H$_5$ 50 mg of FK-506 were dissolved into about 0.5 mL of methylene chloride. About 44 μL of ethyl isocyanoacetate and 42 μL of tributyltin ethoxide were added to the FK-506 solution and stirred at room temperature overnight. The reaction mixture was transferred to a separatory funnel using about 10 ml of methylene chloride and washed three times with about 15 ml of deionized water. The organic layer was dried over sodium sulfate and the solvent removed by rotary evaporation, then dried under high vacuum. The FK-506 esters formed in the reaction were further purified using column chromatography. The solvent was removed by rotary evaporation.

EXAMPLE 2

Preparation of an FK-506 Ester Derivative

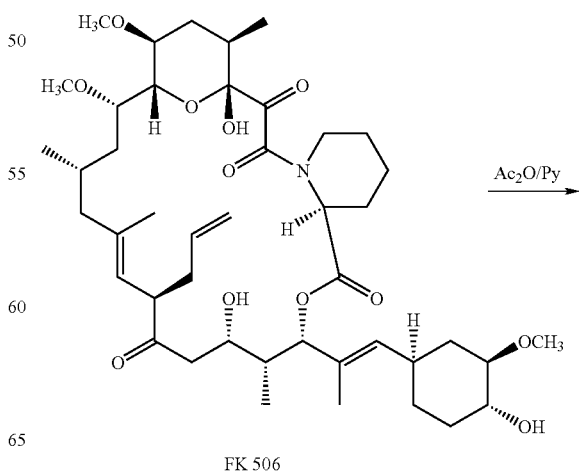

FK 506

-continued

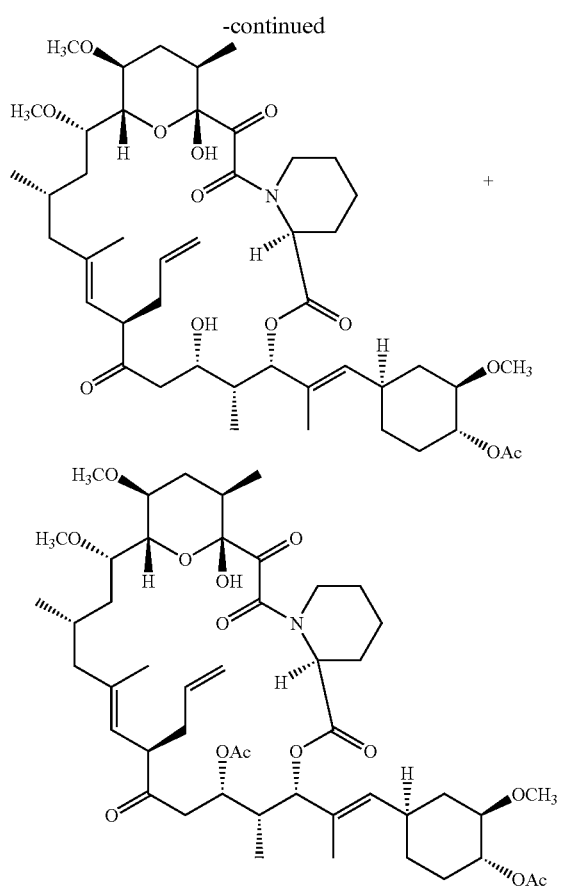

50 mg of FK-506 was dissolved into a solution of 50 μL pyridine in 500 μL of methylene chloride. About 12 μL of acetic anhydride was added to the FK-506 solution and stirred at room temperature for 2 h. The reaction mixture was transferred to a separatory funnel using about 10 mL of methylene chloride and washed three times with about 15 mL of NaHCO$_3$(aq). The organic layer was dried over sodium sulfate and the solvent was removed by rotary evaporation, then dried under high vacuum. The FK-506 residue was further isolated using column chromatography.

EXAMPLE 3

Preparation of FK-506 Carbamate Pretreatment Solution

Stock solution containing 0.45 mg/mL FK-506 ester was prepared by two steps: 1) dissolving 4 mg FK-506 carbamate into 2 mL of methanol. The dissolved FK-506 carbamate is then diluted 1:4.5 with a buffer containing 30 mg/mL protease free bovine serum albumin, 0.126 mg/mL MgCl$_2$, 0.03 mL/mL of Ethylene glycol, 35.14 mg/mL PIPES 1.5 sodium salt, 50 mg/mL NaCl and beta-gal mutein (inactivated beta galactosidase), pH 6.5 to make the stock solution. The stock solution is then diluted to contain 2.7 μg/mL FK carbamate with de-ionized water to make the working pretreatment solution.

Preparation of Anti-FK-506 Antibody-β-galactosidase Conjugate

Monoclonal anti-FK-506 antibody is conjugated to β-galactosidase using standard SMCC (succinimidyl trans-4-(N-maleimidylmethyl)cyclohexane-1-carboxylate) linker. The working antibody conjugate solution contains approximately 7.5 μg/mL anti-FK-506 antibody-β-galactosidase conjugate 30 mg/mL protease free bovine serum albumin, 0.126 mg/mL MgCl$_2$, 0.03mL/mL of Ethylene glycol, 35.14 mg/mL PIPES 1.5 sodium salt, 50 mg/mL NaCl and beta-gal mutein (inactivated beta galactosidase), pH 6.5.

Magnetic Chrome Particle Preparation

The production of FK-506 chrome particles (immunoassay solid phase) proceeds by making the FK-506 -BGG (bovine gammaglobulin)-dextran conjugate, preparing a slurry with the chrome particles and then tabletting the coated particles. Each FK-506 tablets contains approximately 2 mg FK-506 chrome slurry, 10.5 mg 30% bovine serum albumin (BSA), 30.4 mg trehalose dihydrate and 3.6 mg carbowax 100 μm.

Preparation of Rapamycin Pretreatment Solution

Rapamycin was also prepared to serve as the pretreatment reagent to compare to the FK-506 carbamate. The final working solution has the same components and concentrations as the FK-506 carbamate working solution except that 2.7 μg/mL rapamycin was used in place of FK-506 carbamate.

EXAMPLE 4

FK 506 Assay

The measurement of FK 506 used the assay format known as ACMIA and as described in the previous patents (U.S. Pat. Nos. 5,147,529, 5,128,103, 5,158,871, 4,661,408, 5,151,348, 5,302,532, 5,422,284, 5,447,870, 5,434,051). The principle and operation of the FK 506 method are as follows: pretreatment reagent containing the FK 506 carbamate described in this invention is added to the reaction vessel on the DIMENSION® chemistry RxL/HM instrument. Next 35 uLs of whole blood containing FK 506 is added. The whole blood is sampled from a standard cup by first mixing the blood with the ultrasonic sample probe. The mixing of whole blood sample with the FK 506 carbamate pretreatment solution ensures the lysis of the whole blood and the displacement of the protein bound FK 506 molecules from their binding sites by the FK 506 carbamate molecules. The released FK 506 molecules therefore will be accessible to the anti-FK 506 antibody in the reaction mixture. Anti-FK 506 antibody-β-galactosidase conjugate (80 uL) is added next and allowed to react with FK 506 in the sample. The chrome particles with immobilized FK 506-BGG (bovine gamma globulin)-dextran is added (75uL) and allowed to bind the unreacted conjugate. The FK 506 bound Anti-FK 506 antibody-β-galactosidase conjugate does not bind to the chrome but remains in the supernatant when a magnetic field is applied to the above reaction mixture to separate the solution from the chrome particles. The FK 506 bound conjugate is detected by transferring the supernatant from the reaction vessel to a photometric cuvette, and measuring the enzymatic rate of the conjugate in the presence of chlorophenol red-β-D-galactopyranoside (CPRG). The rate is measured bichromatically at 577 and 700 nm. The method schematic is provided in the figure below. Typical calibration curves with and without the FK 506 carbamate pretreatment are compared as shown in FIG. 5.

EXAMPLE 5

Comparison of Different Pretreatment Regimens

FK 506 carbamate, rapamycin, or pretreatment diluent was used to make pretreatment solutions for the DIMENSION® Assay for measuring the FK 506 standards containing 0, 5, 10, 20 and 30 ng/mL FK 506. Another set of FK 506 standards was also treated with the Syva EMIT® pretreatment solutions (200 uL of sample is extracted with 200 uL of methanol and then protein in the mixture is precipitated with 50 uL of cupric sulfate solution. The centrifuged supernatant is used as sample). The standards not treated by the Syva EMIT® reagents were pretreated on board by FK 506 carbamate, rapamycin or the pretreatment only and analyzed on the DIMENSION® clinical chemistry analyzer using the ACMIA assay. The standard pretreated with the Syva EMIT® reagents were tested by the ACMIA assay on a DIMENSION® instrument using reagent cartridges containing only the pretreatment diluent as the pretreatment solution. The following table shows the results obtained by testing these pretreatment approaches.

TABLE 1

| Standards ng/mL FK506 | FK ester ABS × $10^{-3}$ | Rapamycin ABS × $10^{-3}$ | Emit Pretreat ABS × $10^{-3}$ | Pretreat Diluent ABS × $10^{-3}$ |
| --- | --- | --- | --- | --- |
| 0  | 313.7 | 340.2 | 305.9 | 338.2 |
| 5  | 415.6 | 421.3 | 346.3 | 345.2 |
| 10 | 555.6 | 504.4 | 379.1 | 355.8 |
| 20 | 780.2 | 661.3 | 460.2 | 377.2 |
| 30 | 916.2 | 793.1 | 545.6 | 394.6 |

ABS = Absorbance

What is claimed is:

1. A method of determining the presence of a macrophilin-binding pharmaceutical in a sample comprising: adding to the sample a binding competitor of the formula:

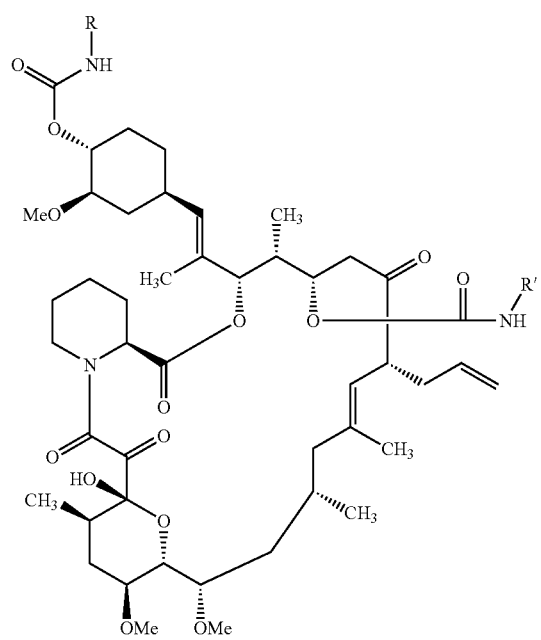

to displace the macrophilin-binding pharmaceutical from its immunophilin complexes wherein R is alkyl, aryl, allyl, each having less than 25 carbons or H, and R' is alkyl, aryl, allyl, each having less than 25 carbons or H; adding a receptor that binds to the pharmaceutical but not significantly to the binding competitor; detecting the receptor-pharmaceutical complex and correlating the detection with the amount of the pharmaceutical in the sample.

2. The method of claim 1 wherein the pharmaceutical is rapamycin (sirolimus), everolimus or tacrolimus (FK506).

3. A method of determining the presence of a macrophilin-binding pharmaceutical in a sample comprising: adding to the sample a binding competitor of the formula:

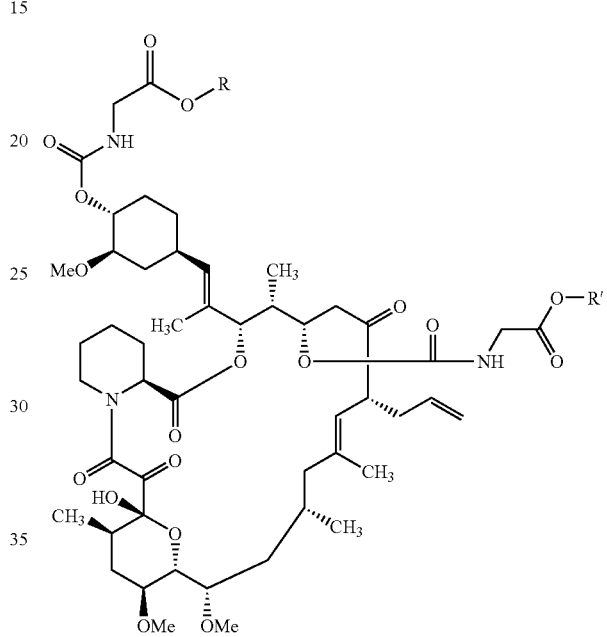

to displace the macrophilin-binding pharmaceutical from its immunophilin complexes wherein R is alkyl, aryl, allyl, each having less than 25 carbons or H, and R' is alkyl, aryl, allyl, each having less than 25 carbons or H; adding a receptor that binds to the pharmaceutical but not significantly to the binding competitor; detecting the receptor-pharmaceutical complex and correlating the detection with the amount of the pharmaceutical in the sample.

4. The method of claim 3 wherein the pharmaceutical is rapamycin (sirolimus), everolimus or tacrolimus (FK506).

5. The method of claim 4 wherein R or R' is ethyl.

6. The method of claim 2 wherein R or R' is ethyl.

7. The method of claim 1 wherein R or R' further comprise at least one functional group selected from the group consisting of esters, ethers, amides, phosphates, sulfonates, sulfate, amidines, phosphonates, amine, hydroxyl or carboxylate functional groups.

8. The method of claim 3 wherein R or R' further comprise at least one functional group selected from the group consisting of esters, ethers, amides, phosphates, sulfonates, sulfate, amidines, phosphonates, amine, hydroxyl or carboxylate functional groups.

* * * * *